(12) United States Patent
Guo et al.

(10) Patent No.: US 9,809,807 B1
(45) Date of Patent: Nov. 7, 2017

(54) CELLULASE HAVING IMPROVED ENZYMATIC ACTIVITY

(71) Applicant: Dongguan APAC Biotechnology CO., Ltd., DongGuan (CN)

(72) Inventors: Rey-Ting Guo, New Taipei (TW); Chun-Chi Chen, New Taipei (TW); Ya-Shan Cheng, New Taipei (TW); Jian-Wen Huang, New Taipei (TW); Tzu-Hui Wu, New Taipei (TW); Hui-Lin Lai, New Taipei (TW); Cheng-Yen Lin, New Taipei (TW); Tsung-Yu Ko, New Taipei (TW)

(73) Assignee: DONGGUAN APAC BIOTECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 15/651,627

(22) Filed: Jul. 17, 2017

(30) Foreign Application Priority Data

Jul. 29, 2016 (TW) .............................. 105124103 A

(51) Int. Cl.
*C12N 9/42* (2006.01)
*C11D 3/386* (2006.01)
*D06M 16/00* (2006.01)
*D21C 5/00* (2006.01)
*C07H 21/00* (2006.01)
*C12N 9/00* (2006.01)

(52) U.S. Cl.
CPC ........ *C12N 9/2437* (2013.01); *C11D 3/38645* (2013.01); *C12Y 302/01004* (2013.01); *D06M 16/003* (2013.01); *D21C 5/005* (2013.01); *C07H 21/00* (2013.01); *C12N 9/00* (2013.01); *D06M 16/00* (2013.01)

(58) Field of Classification Search
CPC .................................................... C12N 9/2437
See application file for complete search history.

(56) References Cited

FOREIGN PATENT DOCUMENTS

WO    WO 2011/109905 A1 *  9/2011

\* cited by examiner

*Primary Examiner* — Suzanne M Noakes
(74) *Attorney, Agent, or Firm* — Kirton McConkie; Evan R. Witt

(57) ABSTRACT

A cellulase having improved enzymatic activity is disclosed. The cellulase comprises a modified amino acid sequence of SEQ ID NO: 2, wherein the modification is a substitution of Tyrosine at position 161 with Histidine.

6 Claims, 7 Drawing Sheets

FIG. 1

| Primer | Primer Sequence |
| --- | --- |
| Y161H F | 5'-TGATGTTATGAACGAACCACATCAAATTGA-3'  (SEQ ID NO: 3) |
| Y161H R | 5'-ACAACAGAAGCGTCAATTTGATGTGGTTCGT-3'  (SEQ ID NO: 4) |

FIG. 2

```
  1 CAGTGCCAACCAGGAGCCGGTCCAACTACAACCTCTTCTGCCCCAAATCCAACTTCTTCTGGATGTCCAAACGCTACTAAGTTTAGATTT  90
    Q  C  Q  P  G  A  G  P  T  T  T  S  S  A  P  N  P  T  S  S  G  C  P  N  A  T  K  F  R  F

91 TTCGGAGTTAATCAGGCTGGTGCAGAATTGGAGAAAACGTCATTCCAGGTGAATTGGGTACTCATTACACTTGGCCTTCTCCATCTTCT  180
    F  G  V  N  Q  A  G  A  E  F  G  E  N  V  I  F  G  E  L  G  T  H  Y  T  W  P  S  P  S  S

181 ATTGATTACTTTGTTAACCAAGGATTTAACACTTTTAGAGTCGCCTTTAAGATCGAAAGATTGTCTCCACCAGGTACTGGTTTGACAGGT  270
    I  D  Y  F  V  N  Q  G  F  N  T  F  R  V  A  F  K  I  E  R  L  S  P  P  G  T  G  L  T  G

271 CCTTTTGATCAGGCATACTTGAACGGATTGAAGACTATTGTCAACTATATTACTGGTAAGAACGCTTACGCAGTTTTGGACCCTCATAAT  360
    P  F  D  Q  A  Y  L  N  G  L  K  T  I  V  N  Y  I  T  G  K  N  A  Y  A  V  L  D  P  H  N

361 TACATGAGATACAACGGTAATGTTATTACCTCTACTTCTAACTTTCAAACTTGGTGGAACAAGTTGGCTACAGAGTTCAGATCTAACACT  450
    Y  M  R  Y  N  G  N  V  I  T  S  T  S  N  F  Q  T  W  W  N  K  L  A  T  E  F  R  S  N  T

451 AGAGTTATCTTTGATGTTATGAACGAACCACATCAAATTGACGCTTCTGTTGTTTTTAACTTGAATCAAGCCGCTATTAATGGAATTAGA  540
    R  V  I  F  D  V  M  N  E  P  H  Q  I  D  A  S  V  V  F  N  L  N  Q  A  A  I  N  G  I  R

541 GCCTCTGGTGCCACTTCTCAGTTGATTTTGGTTGAAGGAACTGCATGGACAGGTGCTTGGTCTTGGGAATCTTCTGGAAATGGTGCTGTT  630
    A  S  G  A  T  S  Q  L  I  L  V  E  G  T  A  W  T  G  A  W  S  W  E  S  S  G  N  G  A  V

631 TTTGGTGCTATCAGAGATCCAAATAACAATACTGCTATTGAAATGCATCAGTACTTGGATTCTGATTCTTCTGGTACTTCTGCTACTTGC  720
    F  G  A  I  R  D  P  N  N  N  T  A  I  E  M  H  Q  Y  L  D  S  D  S  S  G  T  S  A  T  C

721 GTCTCTTCTACTGTTGGAGTTGAGAGATTGAGAGTTGCCACTGACTGGTTGAGAAGAAACAATTTGAAGGGTTTTTTGGGTGAAATGGGT  810
    V  S  S  T  V  G  V  E  R  L  R  V  A  T  D  W  L  R  R  N  N  L  K  G  F  L  G  E  M  G

811 GCCGGATCTAATGATGTCTGTATTGCTGCCGTTAAGGGTGCTTTGTGTGCTATGCAACAATCTGGTGTTTGGATTGGTTACTTGTGGTGG  900
    A  G  S  N  D  V  C  I  A  A  V  K  G  A  L  C  A  M  Q  Q  S  G  V  W  I  G  Y  L  W  W

901 GCTGCTGGTCCTTGGTGGGGTACTTACTTCCAATCTATCGAGCCACCTAACGGTGCTTCTATCGCTAGAATTTTGCCAGAGGCTTTGAAG  990
    A  A  G  P  W  W  G  T  Y  F  Q  S  I  E  P  P  N  G  A  S  I  A  R  I  L  P  E  A  L  K

991 CCATTTGTTTAA 1002    -SEQ ID NO: 5
    P  F  V  *           -SEQ ID NO: 6
```

FIG. 3

CELLULASE HAVING IMPROVED ENZYMATIC ACTIVITY

FIELD OF THE INVENTION

The present invention relates to a cellulase, and more particularly to a cellulase having improved enzymatic activity.

BACKGROUND OF THE INVENTION

Cellulose is one of the major components in plant cell wall and is also a major resource of biomass on earth. Hence, many enzymes that degrade cellulose can be widely applied in many different industries. Cellulose is a polysaccharide composed of glucose units linked by β-1,4-glycosidic bond. These polysaccharides organize tightly together to form crystalline cellulose in order to defense destructing energy from outside of plant. On the other hand, many kinds of herbivores and microbes need to degrade cellulose from plant to glucose as an energy source by different degrading enzymes including cellulase, xylanase and so on. The catalytic mechanism of cellulase involves hydrolyzing the β-1, 4-glycosidic bond between two sugar units by acid-base interaction. Cellulase can be generally divided into three groups including endoglucanase, cellobiohydrolase and β-glucosidase. Endoglucanase can randomly degrade cellulose into many small fragments. Cellobiohydrolase can degrade cellulose from reducing end or non-reducing end to release main product, cellobiose. β-Glucosidase can degrade cellobiose into simple sugar glucose.

So far, the industrial applications of cellulase are widespread in food industry, feed industry or textile industry, even in biofuel production. In general, cellulase needs to conform to different appropriate conditions according to different industrial needs. For example, acidic and thermostable enzymes are suitable for the feed industry but textile industry prefers alkaline enzymes. Therefore, scientists always try to seek better enzymes which are more suitable for different industrial needs in academic or industrial researches. Currently, many researchers and enzyme companies could produce better enzymes by screening in nature or modifying present enzymes. There are generally two strategies of enzyme modification including directed evolution that randomly mutates the enzyme gene and selects with desirable properties and rationale engineering that specifically mutates the enzyme gene based on the structural information of the enzyme.

Therefore, the present invention intends to analyze the enzyme structure of the cellulase for finding out the key amino acid important to the enzymatic activity and further modify the enzyme, so as to improve the enzymatic activity of the cellulase and thus increase the industrial value of the cellulase.

SUMMARY OF THE INVENTION

An object of the present invention is to modify a cellulase by means of structural analysis and site-directed mutagenesis for efficiently improving the enzymatic activity and further increasing the industrial value of the cellulase.

According to an aspect of the present invention, there is provided a cellulase comprising a modified amino acid sequence of SEQ ID NO: 2, wherein the modification is a substitution of Tyrosine at position 161 with Histidine.

In an embodiment, a gene encoding the amino acid sequence of SEQ ID NO: 2 is eg1t gene isolated from *Volvariella volvacea* and optimized.

In an embodiment, the cellulase is an endoglucanase.

In an embodiment, the cellulase has a full length amino acid sequence of SEQ ID NO: 6.

According to another aspect of the present invention, there is provided a nucleic acid encoding the aforesaid cellulase, and a recombinant plasmid comprising the aforesaid nucleic acid.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the nucleotide sequence and the amino acid sequence of the wild-type eg1t cellulase;

FIG. 2 shows the primer sequences for site-directed mutagenesis;

FIG. 3 shows the nucleotide sequence and the amino acid sequence of the mutant cellulase Y161H;

DETAILED DESCRIPTION OF THE PREFERRED EMBODIMENT

Figure 4:
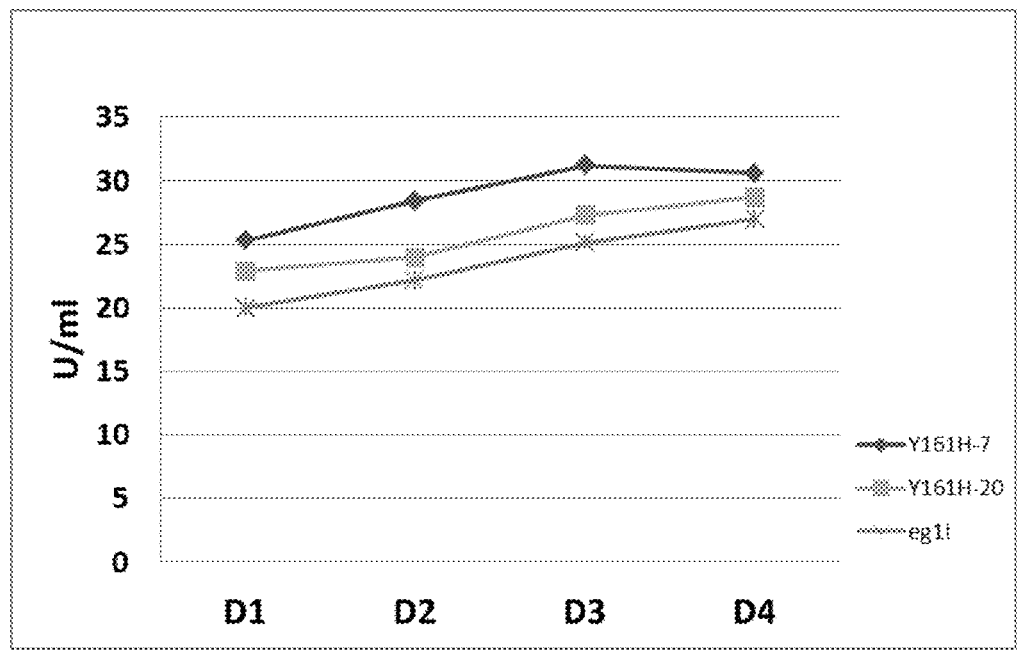
FIG. 4 shows the activity analysis of the wild-type eg1t and the Y161H mutant in BMMY flask.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The endoglucanase gene Cel5A from *Trichoderma reesei* encodes a cellulase with high enzymatic activity, and thus the Cel5A protein is one of the most common cellulases which are studied, modified and applied in textile industry. The cellulase employed in the present invention is encoded by the endoglucanase gene eg1t isolated from *Volvariella volvacea*. The protein structure of eg1t obtained from computer modeling was compared with the Cel5A protein to find out the consensus residues and then select the amino acid near the active site that may influence the enzymatic activity for further modification.

The enzyme modification processes and the resulted cellulase protein are described in detail as follows.

First, the amino acid sequence of the endoglucanase eg1t from *Volvariella volvacea* was used for protein structure modeling by SWISS-MODEL. Then the modeled protein structure of eg1t from *Volvariella volvacea* was further analyzed by PyMOL for alignment with the Cel5A protein (PDB ID: 3QR3) from *Trichoderma reesei*. It was found that in the protein structure of Cel5A from *Trichoderma reesei*, there is a stacking between the Histidine (H) at position 150 and the Tryptophan (W) at position 185 near the active site, which may influence the enzymatic activity. While in the protein structure of eg1t from *Volvariella volvacea*, the corresponding structure is located between the Tyrosine (Y) at position 161 and the Tryptophan (W) at position 252.

Therefore, the present invention intends to substitute the Tyrosine (Y) at position 161 of the eg1t protein with Histidine (H), and express the mutant protein Y161H for activity analysis.

Figure 1:
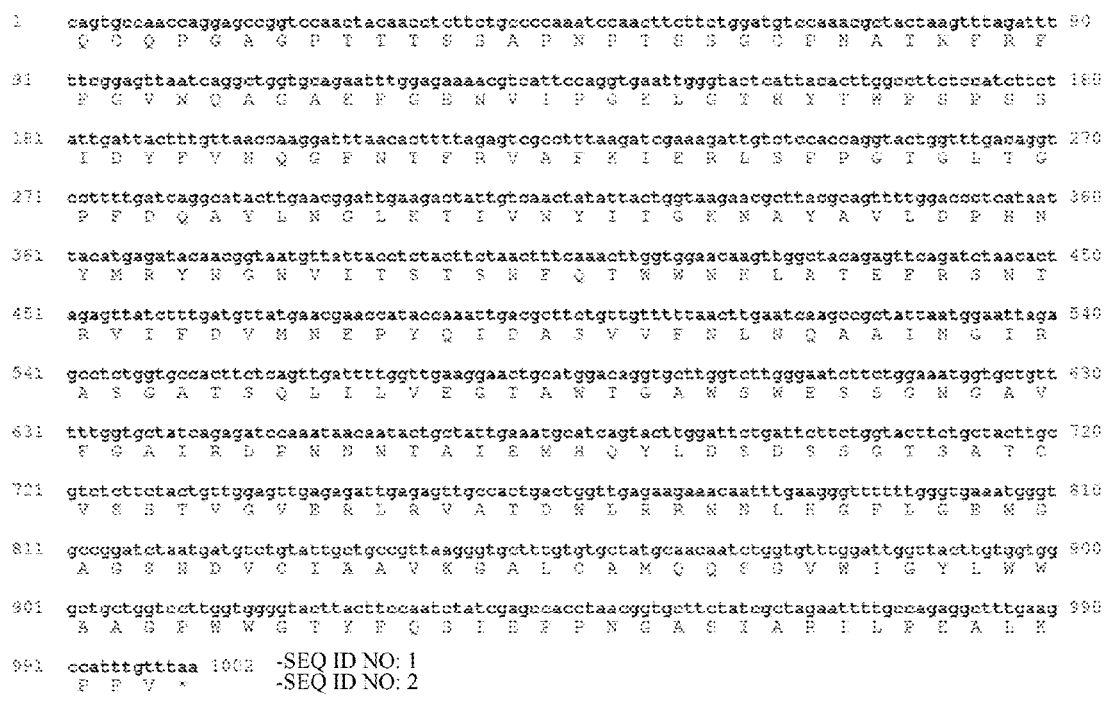

The modification was performed by site-directed mutagenesis. First, the endoglucanase eg1t gene is constructed and optimized. FIG. 1 shows the nucleotide sequence and the amino acid sequence of the wild-type eg1t cellulase, wherein the eg1t cellulase gene consists of 1002 base pairs (SEQ ID NO: 1, including the stop codon) and encodes 333 amino acids (SEQ ID NO: 2). The eg1t gene was constructed into pPICZαA vector by EcoRI and NotI. FIG. 2 shows the primer sequences for site-directed mutagenesis to substitute the Tyrosine (Y) at position 161 of the eg1t protein with Histidine (H), wherein F represents the forward primer which was numbered as SEQ ID NO: 3, and R represents the reverse primer which was numbered as SEQ ID NO: 4. FIG. 3 shows the nucleotide sequence and the amino acid sequence of the mutant cellulase Y161H, wherein the mutant cellulase Y161H gene also consists of 1002 base pairs (SEQ ID NO: 5, including the stop codon) and encodes 333 amino acids (SEQ ID NO: 6), and the Tyrosine (Y) at position 161 was substituted with Histidine (H).

The modified DNA plasmids were linearized by PmeI and then transformed into *Pichia pastoris* X33 by electroporation. The transformants were selected on YPD plates containing 100 µg/ml zeocin and cultured at 30° C. for 2 days. The selected colonies were inoculated in 5 ml of YPD at 30° C. and then amplified in 50 ml of BMGY at 30° C. for 24 hours. The cells were harvested and then resuspended in 20 ml of BMMY to induce protein expression for 4 days. The samples were collected at different time points for every 24 hours, and meanwhile, the methanol was added into the flask to the final concentration of 0.5%. The cells were harvested by centrifugation at 3500 rpm and the supernatant was collected for protein purification and activity determination.

The cellulase activity was determined as follows. The reaction was started by mixing 0.2 ml of 1% carboxymethyl cellulose (CMC, pH 6.0, 0.05 M potassium phosphate buffer) and 0.2 ml of the cellulase protein solution at a proper concentration diluted in 0.05 M potassium phosphate buffer, pH 6.0. After incubation at 50° C. for 15 min, the reaction was stopped by adding 1.2 ml of 1% DNS reagent and incubation in 100° C. boiled water for 5 min. After cooled down in cold water bath for 10 min, the absorption of OD540 was detected and the enzymatic activity was determined. The standard curve of the enzymatic activity was determined by 0-0.35 µg/ml glucose standard solution, and one unit was defined as the enzyme level that could release 1 µmole product per minute.

FIG. 4 shows the activity analysis of the wild-type eg1t and the Y161H mutant in BMMY flask. The supernatants of the two expression strains Y161H-7 and Y161H-20 were selected for activity analysis. It was observed that the cellulase activities of the mutants Y161H-7 and Y161H-20 were both higher than that of the wild-type eg1t after methanol induction in day 1 (D1) to day 4 (D4).

Figure 5:
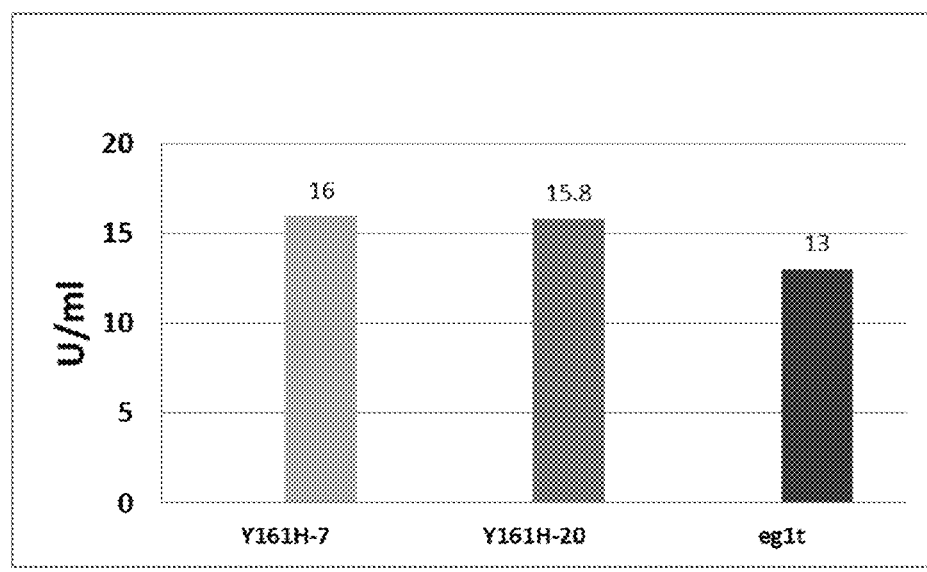
FIG. 5 shows the activity analysis of the wild-type eg1t and the Y161H mutant with the same protein concentration.

The enzyme concentrations of the mutants Y161H-7 and Y161H-20 and the wild-type eg1t were further adjusted to be consistent with each other. Then the enzymatic activities were determined in 0.05 M potassium phosphate buffer, pH 6.0 and at 50° C., and the relative enzymatic activities were compared. FIG. 5 shows the activity analysis of the wild-type eg1t and the Y161H mutant with the same protein concentration. It was observed from FIG. 5 that the cellulase activities of the mutants Y161H-7 and Y161H-20 were both significantly higher than that of the wild-type eg1t when the enzymatic activities were determined with the same protein concentration.

Figure 6:
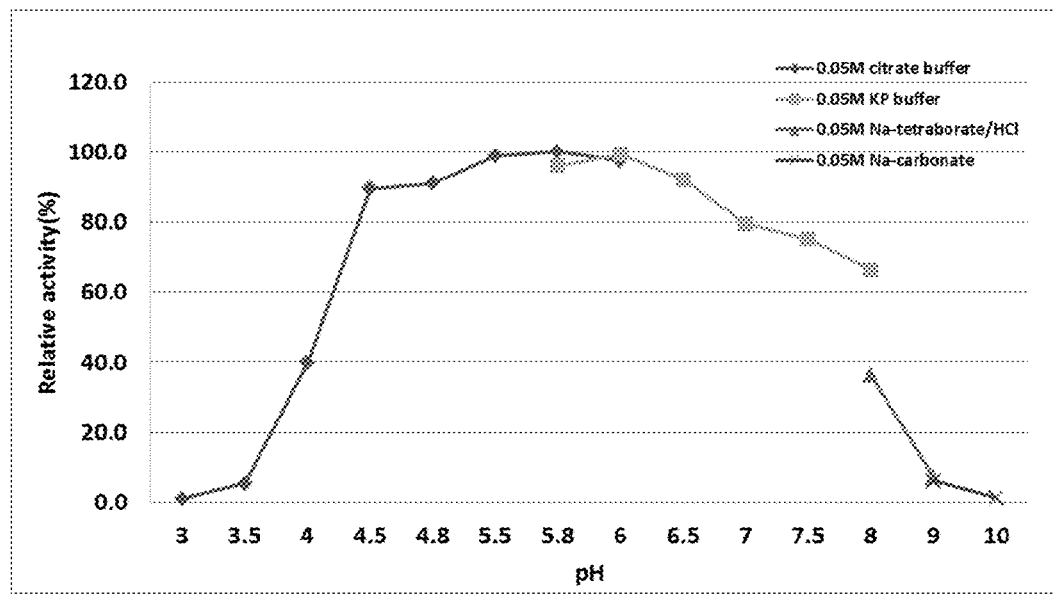
FIG. 6 shows the optimal pH values of the wild-type eg1t.
Figure 7:
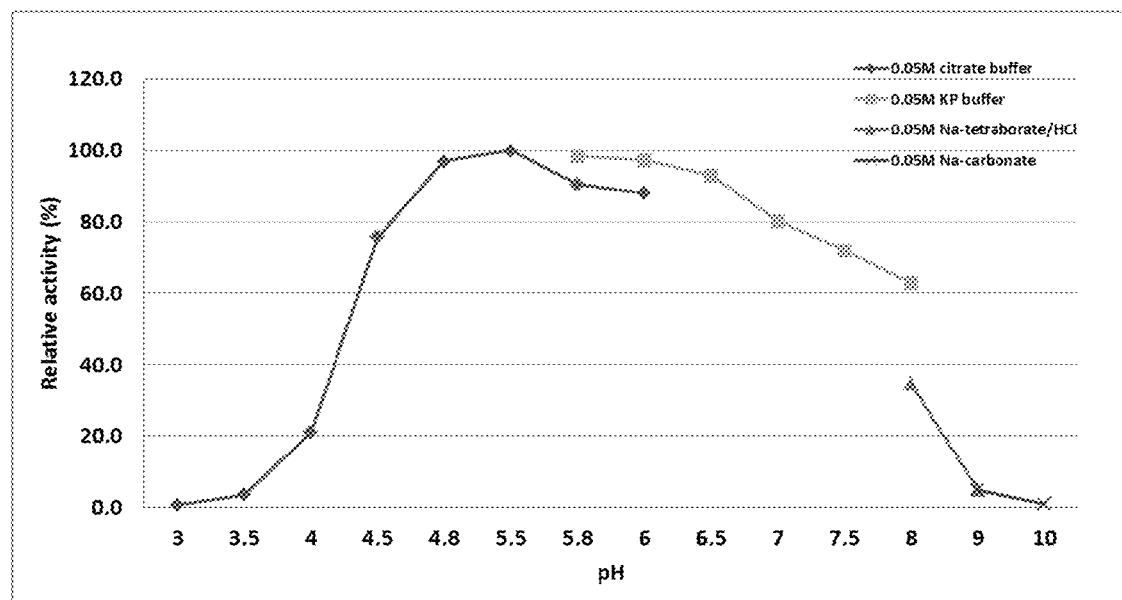
FIG. 7 shows the optimal pH values of the Y161H mutant.

In addition, the optimal pH values of the wild-type eg1t and the Y161H mutant were also analyzed. The cellulase protein solutions at proper concentrations were diluted in different buffers, including 0.05 M citrate buffer at pH 3.5~pH 6.0, 0.05 M potassium phosphate buffer (KP buffer) at pH 5.8~pH 8.0, 0.05 M Na-tetraborate/HCl buffer at pH 8.0~pH 9.0, and 0.05 M Na-carbonate buffer at pH 9.0~pH 10. After incubation at 50° C. for 15 min, the samples were cooled down at 4° C. for 10 min and then stayed at room temperature for 10 min. Afterward, the enzymatic activities at 50° C. were determined, and the relative activities under different pH values, compared to the highest activity as 100%, were further analyzed. FIG. 6 shows the optimal pH values of the wild-type eg1t, and FIG. 7 shows the optimal pH values of the Y161H mutant. From the result, it was observed that the optimal pH values of the Y161H mutant were not different from the optimal pH values of the wild-type eg1t, and both were ranged from pH 5.5~pH 5.8.

In conclusion, to increase the industrial value of the cellulase, the present invention compared the protein structures of the eg1t from *Volvariella volvacea* and the Cel5A from *Trichoderma reesei* to screen the mutation residue near the active site. The Tyrosine (Y) at position 161 of the eg1t from *Volvariella volvacea* was substituted with Histidine (H), and the Y161H mutant was expressed for further analysis. It was observed that the cellulase activity of the Y161H mutant was significantly higher than that of the wild-type eg1t, and the optimal pH values of the Y161H mutant did not change. Therefore, the Y161H mutant provided in the present invention has improved cellulase activity, so the production cost can be reduced and industrial values are further increased.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A cellulase comprising a modified amino acid sequence of SEQ ID NO: 2, wherein the modification is a substitution of Tyrosine at position 161 with Histidine.

2. The cellulase according to claim 1 wherein a gene encoding the amino acid sequence of SEQ ID NO: 2 is eg1t gene isolated from *Volvariella volvacea* and optimized.

3. The cellulase according to claim 1 being an endoglucanase.

4. The cellulase according to claim 1 having a full length amino acid sequence of SEQ ID NO: 6.

5. A nucleic acid encoding the cellulase of claim 1.

6. A recombinant plasmid comprising the nucleic acid of claim 5.

* * * * *

SEQUENCE LISTING

```
<160> NUMBER OF SEQ ID NOS: 6

<210> SEQ ID NO 1
<211> LENGTH: 1002
<212> TYPE: DNA
<213> ORGANISM: Volvariella volvacea

<400> SEQUENCE: 1
```

-continued

```
cagtgccaac caggagccgg tccaactaca acctcttctg ccccaaatcc aacttcttct    60
ggatgtccaa acgctactaa gtttagattt ttcggagtta atcaggctgg tgcagaattt   120
ggagaaaacg tcattccagg tgaattgggt actcattaca cttggccttc tccatcttct   180
attgattact ttgttaacca aggatttaac acttttagag tcgcctttaa gatcgaaaga   240
ttgtctccac caggtactgg tttgacaggt ccttttgatc aggcatactt gaacggattg   300
aagactattg tcaactatat tactggtaag aacgcttacg cagttttgga ccctcataat   360
tacatgagat acaacggtaa tgttattacc tctacttcta actttcaaac ttggtggaac   420
aagttggcta cagagttcag atctaacact agagttatct ttgatgttat gaacgaacca   480
taccaaattg acgcttctgt tgtttttaac ttgaatcaag ccgctattaa tggaattaga   540
gcctctggtg ccacttctca gttgattttg gttgaaggaa ctgcatggac aggtgcttgg   600
tcttgggaat cttctggaaa tggtgctgtt tttggtgcta tcagagatcc aaataacaat   660
actgctattg aaatgcatca gtacttggat tctgattctt ctggtacttc tgctacttgc   720
gtctcttcta ctgttggagt tgagagattg agagttgcca ctgactggtt gagaagaaac   780
aatttgaagg ttttttgggt gaaatgggt gccggatcta atgatgtctg tattgctgcc   840
gttaagggtg ctttgtgtgc tatgcaacaa tctggtgttt ggattggtta cttgtggtgg   900
gctgctggtc cttggtgggg tacttacttc caatctatcg agccacctaa cggtgcttct   960
atcgctagaa ttttgccaga ggctttgaag ccatttgttt aa                     1002
```

<210> SEQ ID NO 2
<211> LENGTH: 333
<212> TYPE: PRT
<213> ORGANISM: Volvariella volvacea

<400> SEQUENCE: 2

```
Gln Cys Gln Pro Gly Ala Gly Pro Thr Thr Thr Ser Ser Ala Pro Asn
1               5                   10                  15

Pro Thr Ser Ser Gly Cys Pro Asn Ala Thr Lys Phe Arg Phe Phe Gly
            20                  25                  30

Val Asn Gln Ala Gly Ala Glu Phe Gly Glu Asn Val Ile Pro Gly Glu
        35                  40                  45

Leu Gly Thr His Tyr Thr Trp Pro Ser Pro Ser Ser Ile Asp Tyr Phe
    50                  55                  60

Val Asn Gln Gly Phe Asn Thr Phe Arg Val Ala Phe Lys Ile Glu Arg
65                  70                  75                  80

Leu Ser Pro Pro Gly Thr Gly Leu Thr Gly Pro Phe Asp Gln Ala Tyr
                85                  90                  95

Leu Asn Gly Leu Lys Thr Ile Val Asn Tyr Ile Thr Gly Lys Asn Ala
            100                 105                 110

Tyr Ala Val Leu Asp Pro His Asn Tyr Met Arg Tyr Asn Gly Asn Val
        115                 120                 125

Ile Thr Ser Thr Ser Asn Phe Gln Thr Trp Trp Asn Lys Leu Ala Thr
    130                 135                 140

Glu Phe Arg Ser Asn Thr Arg Val Ile Phe Asp Val Met Asn Glu Pro
145                 150                 155                 160

Tyr Gln Ile Asp Ala Ser Val Val Phe Asn Leu Asn Gln Ala Ala Ile
                165                 170                 175

Asn Gly Ile Arg Ala Ser Gly Ala Thr Ser Gln Leu Ile Leu Val Glu
            180                 185                 190
```

```
Gly Thr Ala Trp Thr Gly Ala Trp Ser Trp Glu Ser Gly Asn Gly
            195                 200                 205

Ala Val Phe Gly Ala Ile Arg Asp Pro Asn Asn Thr Ala Ile Glu
        210                 215                 220

Met His Gln Tyr Leu Asp Ser Asp Ser Ser Gly Thr Ser Ala Thr Cys
225                 230                 235                 240

Val Ser Ser Thr Val Gly Val Glu Arg Leu Arg Val Ala Thr Asp Trp
                245                 250                 255

Leu Arg Arg Asn Asn Leu Lys Gly Phe Leu Gly Glu Met Gly Ala Gly
            260                 265                 270

Ser Asn Asp Val Cys Ile Ala Ala Val Lys Gly Ala Leu Cys Ala Met
        275                 280                 285

Gln Gln Ser Gly Val Trp Ile Gly Tyr Leu Trp Trp Ala Ala Gly Pro
    290                 295                 300

Trp Trp Gly Thr Tyr Phe Gln Ser Ile Glu Pro Pro Asn Gly Ala Ser
305                 310                 315                 320

Ile Ala Arg Ile Leu Pro Glu Ala Leu Lys Pro Phe Val
                325                 330

<210> SEQ ID NO 3
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 3
tgatgttatg aacgaaccac atcaaattga                                30

<210> SEQ ID NO 4
<211> LENGTH: 31
<212> TYPE: DNA
<213> ORGANISM: Artificial Sequence
<220> FEATURE:
<223> OTHER INFORMATION: Synthetically generated primer

<400> SEQUENCE: 4
acaacagaag cgtcaatttg atgtggttcg t                              31

<210> SEQ ID NO 5
<211> LENGTH: 1002
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 5
cagtgccaac caggagccgg tccaactaca acctcttctg ccccaaatcc aacttcttct    60
ggatgtccaa cgctactaa gtttagattt ttcggagtta atcaggctgg tgcagaattt    120
ggagaaaacg tcattccagg tgaattgggt actcattaca cttggccttc tccatcttct   180
attgattact tgttaaccca aggatttaac acttttagag tcgcctttaa gatcgaaaga   240
ttgtctccac caggtactgg tttgacaggt ccttttgatc aggcatactt gaacggattg   300
aagactattg tcaactatat tactggtaag aacgcttacg cagttttgga ccctcataat   360
tacatgagat acaacggtaa tgttattacc tctacttcta actttcaaac ttggtggaac   420
aagttggcta cagagttcag atctaacact agagttatct tgatgttat gaacgaacca    480 catcaaattg acgcttctgt tgtttttaac ttgaatcaag ccgctattaa tggaattaga   540
```

-continued

```
gcctctggtg ccacttctca gttgattttg gttgaaggaa ctgcatggac aggtgcttgg    600
tcttgggaat cttctggaaa tggtgctgtt tttggtgcta tcagagatcc aaataacaat    660
actgctattg aaatgcatca gtacttggat tctgattctt ctggtacttc tgctacttgc    720
gtctcttcta ctgttggagt tgagagattg agagttgcca ctgactggtt gagaagaaac    780
aatttgaagg ttttttggg tgaaatgggt gccggatcta atgatgtctg tattgctgcc    840
gttaagggtg ctttgtgtgc tatgcaacaa tctggtgttt ggattggtta cttgtggtgg    900
gctgctggtc cttggtgggg tacttacttc caatctatcg agccacctaa cggtgcttct    960
atcgctagaa ttttgccaga ggctttgaag ccatttgttt aa                      1002
```

<210> SEQ ID NO 6
<211> LENGTH: 333
<212> TYPE: PRT
<213> ORGANISM: Artificial Sequence
<220> FEATURE:
<223> OTHER INFORMATION: Sequence synthetically translated from SEQ ID NO: 5

<400> SEQUENCE: 6

```
Gln Cys Gln Pro Gly Ala Gly Pro Thr Thr Thr Ser Ser Ala Pro Asn
1               5                   10                  15

Pro Thr Ser Ser Gly Cys Pro Asn Ala Thr Lys Phe Arg Phe Phe Gly
            20                  25                  30

Val Asn Gln Ala Gly Ala Glu Phe Gly Glu Asn Val Ile Pro Gly Glu
        35                  40                  45

Leu Gly Thr His Tyr Thr Trp Pro Ser Pro Ser Ser Ile Asp Tyr Phe
    50                  55                  60

Val Asn Gln Gly Phe Asn Thr Phe Arg Val Ala Phe Lys Ile Glu Arg
65                  70                  75                  80

Leu Ser Pro Pro Gly Thr Gly Leu Thr Gly Pro Phe Asp Gln Ala Tyr
                85                  90                  95

Leu Asn Gly Leu Lys Thr Ile Val Asn Tyr Ile Thr Gly Lys Asn Ala
            100                 105                 110

Tyr Ala Val Leu Asp Pro His Asn Tyr Met Arg Tyr Asn Gly Asn Val
        115                 120                 125

Ile Thr Ser Thr Ser Asn Phe Gln Thr Trp Trp Asn Lys Leu Ala Thr
    130                 135                 140

Glu Phe Arg Ser Asn Thr Arg Val Ile Phe Asp Val Met Asn Glu Pro
145                 150                 155                 160

His Gln Ile Asp Ala Ser Val Val Phe Asn Leu Asn Gln Ala Ala Ile
                165                 170                 175

Asn Gly Ile Arg Ala Ser Gly Ala Thr Ser Gln Leu Ile Leu Val Glu
            180                 185                 190

Gly Thr Ala Trp Thr Gly Ala Trp Ser Trp Glu Ser Ser Gly Asn Gly
        195                 200                 205

Ala Val Phe Gly Ala Ile Arg Asp Pro Asn Asn Thr Ala Ile Glu
    210                 215                 220

Met His Gln Tyr Leu Asp Ser Asp Ser Ser Gly Thr Ser Ala Thr Cys
225                 230                 235                 240

Val Ser Ser Thr Val Gly Val Glu Arg Leu Arg Val Ala Thr Asp Trp
                245                 250                 255

Leu Arg Arg Asn Asn Leu Lys Gly Phe Leu Gly Glu Met Gly Ala Gly
            260                 265                 270
```

```
Ser Asn Asp Val Cys Ile Ala Ala Val Lys Gly Ala Leu Cys Ala Met
        275                 280                 285

Gln Gln Ser Gly Val Trp Ile Gly Tyr Leu Trp Trp Ala Ala Gly Pro
    290                 295                 300

Trp Trp Gly Thr Tyr Phe Gln Ser Ile Glu Pro Pro Asn Gly Ala Ser
305                 310                 315                 320

Ile Ala Arg Ile Leu Pro Glu Ala Leu Lys Pro Phe Val
                325                 330
```